United States Patent [19]

Gosis et al.

[11] Patent Number: 4,620,105
[45] Date of Patent: Oct. 28, 1986

[54] DEVICE FOR ATTACHING A COLLIMATOR TO A RADIATION DETECTOR

[76] Inventors: Anatoly I. Gosis, 552 Burno Dr., Palatine, Ill. 60067; Margaret Fialko, 8835 Mango, Morton Grove, Ill. 60053; George J. Hanz, 254 Thrasher, Bloomingdale, Ill. 60108

[21] Appl. No.: 588,845

[22] Filed: Mar. 12, 1984

[51] Int. Cl.$^4$ .......................... G01B 5/00; G21K 1/02
[52] U.S. Cl. ................................... 250/505.1; 378/148
[58] Field of Search ................. 250/363 SB, 363 SC, 250/363 SF, 505.1; 378/91, 114, 148, 149, 151; 354/286

[56] References Cited

U.S. PATENT DOCUMENTS 3,024,510  3/1962  Malesko .
3,906,534  9/1975  Shirasaki ........................... 354/286
4,129,784 12/1978  Tschunt et al. .
4,217,064  8/1980  Hogan .
4,239,364 12/1980  Doi .................................... 354/286

FOREIGN PATENT DOCUMENTS 0066329 12/1982 European Pat. Off. .
888677   1/1962 United Kingdom .

OTHER PUBLICATIONS

Simple and Efficient System for Fast Interchange of Low-Energy Collimators, Malamud and Sham, Journal of Nuclear Medicine (USA) Dec. 1975, vol. 16, No. 12, pp. 1195-1196.
Brochure PHO/Gamma ® ZLC ™ Standard Camera of Searle Radiographics, 1980, RR28010M512.

Primary Examiner—Alfred E. Smith

[57] ABSTRACT

A device for attaching a collimator to a radiation detector. A number of cleats are mounted at the radiation detector for cleating the collimator to the radiation detector and a latch means serves for latching the cleated collimator against rotation. Also a collimator cleating detection means is associated with the cleat means for detecting incorrect cleating of the collimator and a collimator latch detection means is associated with the latch means for detecting incorrect latching of the collimator.

17 Claims, 8 Drawing Figures

DEVICE FOR ATTACHING A COLLIMATOR TO A RADIATION DETECTOR

BACKGROUND OF THE INVENTION

1. Field of the Invention

The invention relates to a device for attaching a collimator to a radiation detector. In particular, the radiation detector is part of a scintillation gamma camera for nuclear diagnosis purposes.

2. Description of the Prior Art

Conventional radiation detectors (e.g. in scintillation gamma cameras of Siemens Gammasonics, Inc., 2000 Nuclear Drive, Des Plaines, Ill. 60018) comprise a number of cleats for cleating the collimator to the radiation detector. They also comprise a spring-loaded lever-like latch for latching the cleated collimator against rotation. The lever-like latch is rotatable between a first position, where it does not latch the collimator and a second position, where it latches the collimator. These prior art cleats and latch devices for attaching a collimator to a radiation detector are technically simple and easy to operate. However, it depends alone on the individual carefulness of the medical personnel to correctly attach a collimator to a radiation detector.

Other conventional detector heads (e.g. brochure PHO/Gamma® ZLC ™ Standard Camera of Seale Radiographics, 1980, RR28010M512) utilize screws for screwing the collimator to the radiation detector. Each screw is also part of a radiation detector locking system. In case a screw is not in the right end position for attaching the collimator to the radiation detector, the radiation detector would become automatically locked against any kind of movement.

This prior art device for attaching a collimator to a radiation detector is technically relatively complicated and difficult to operate.

SUMMARY OF THE INVENTION

1. Objects

It is an object of this invention to provide a device for attaching a collimator to a radiation detector which is technically simple and easy to operate and which is especially safe with regard to faulty collimator attaching.

2. Summary

According to this invention a device for attaching a collimator to a radiation detector is provided, which comprises
  (a) a cleat means at the radiation detector for cleating the collimator to the radiation detector;
  (b) a latch means for latching the cleated collimator against rotation;
  (c) a collimator cleating detection means associated with the cleat means for detecting incorrect cleating of the collimator; and
  (d) a collimator latching detection means associated with the latch means for detecting incorrect latching of the collimator.

The attaching device according to the invention comprises cleat means and latch means. Therefore, it is technically simple and easy to operate. In addition to this, the attaching device according to this invention also comprises collimator cleating detection means and collimator latching detecting means which detect incorrect cleating or latching of the collimator. Under these circumstances, the attaching device according to the invention is also safe against faulty collimator attaching.

In a preferred embodiment the cleat means comprises a number of cleats and the collimator cleating detection means includes
  (a) a cleat switch means for each cleat designated for being activated by the collimator during collimator cleating; and
  (b) a logic circuit means connected with each cleat switch means for generating a detection signal when at least one cleat switch means has not been activated by the collimator during collimator cleating.

In case the collimator is incorrectly attached to at least one cleat this will immediately be detected by the logic circuit.

In another preferred embodiment the latch means are movable between a first position, where the latch means does not latch the collimator and a second position, where the latch means latches the collimator, and the collimator latching detection means include
  (a) a first latch switch means for the latch means designated for being activated by the collimator during collimator cleating;
  (b) a second latch switch means for the latch means designated for being activated by the latch means in the second latch means position; and
  (c) a logic circuit means connected with the first and second latch switch means for generating a detection signal when one of the first and second latch switch means has been activated while the other one has not been activated.

In this case, if the collimator is incorrectly cleated the logic circuit will detect this fault, also when the latch means do correctly latch the collimator. However, detection is also made in case that the latch means are already in latch position before cleating of the collimator. The latch means such become better protected against violent destruction. Also, if the collimator is correctly cleated, however instead, if the latch means do not correctly latch, the logic circuit will detect this fault.

In still another preferred embodiment the aforementioned preferred embodiments in combination comprise a logic circuit means connected with a cleat and latch switch means for generating a detection signal, when
  (e1) at least one cleat switch means has not been activated by the collimator during collimator cleating; or
  (e2) each cleat switch means has been activated by the collimator during collimator cleating while the latch switch means has not been activated.

This embodiment combines in technically simple manner all the aforementioned advantages.

According to another aspect of this invention also a device for attaching a collimator to a radiation detector is provided, which comprises
  (a) a cleat means at the radiation detector for cleating the collimator to the radiation detector; and
  (b) a latch means for latching the cleated collimator against rotation;
wherein the latch means includes a collimator latch lock mounted at the radiation detector and a rotary cam mounted at the collimator for additionally wedging the collimator in the cleat means.

In this case the collimator latch lock will be the main lock for preventing the cleated collimator from rotation, such that it cannot unintentionally fall off the radiation detector. Wedging by means of the rotary cam provides additional protection. The collimator sits firmly in the cleats since the rotary cam compensates for tolerances of the cleats.

The foregoing and other objects, features and advantages of the invention will be apparent from the following more particular description of preferred embodiments of the invention, as illustrated in the accompanying drawings.

DETAILED DESCRIPTION OF THE PREFERRED EMBODIMENT

Figure 1:
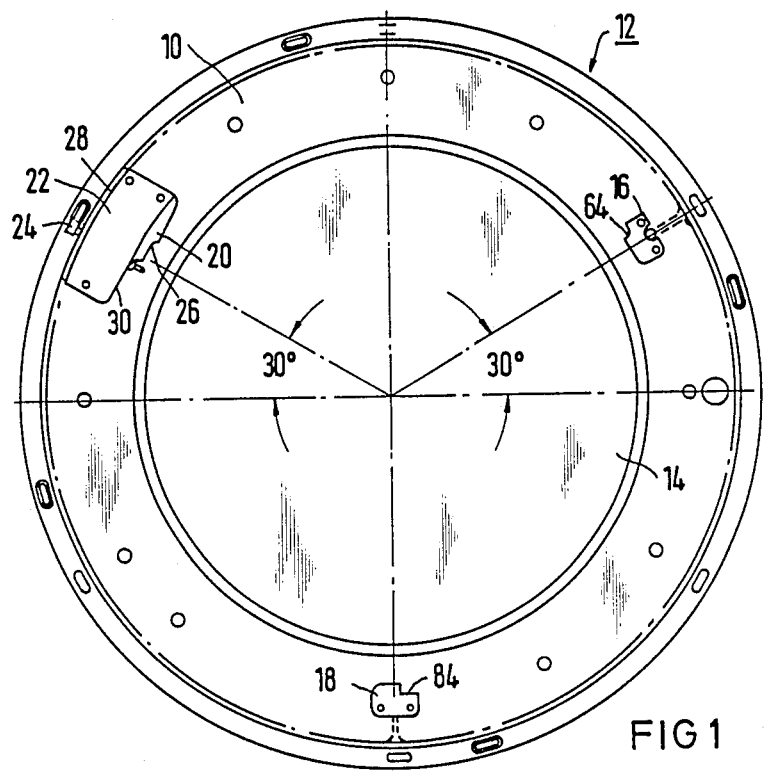
FIG. 1 is a top view of the face of a scintillation gamma camera radiation detector which comprises a device for attaching a collimator according to this invention.
Figure 7:
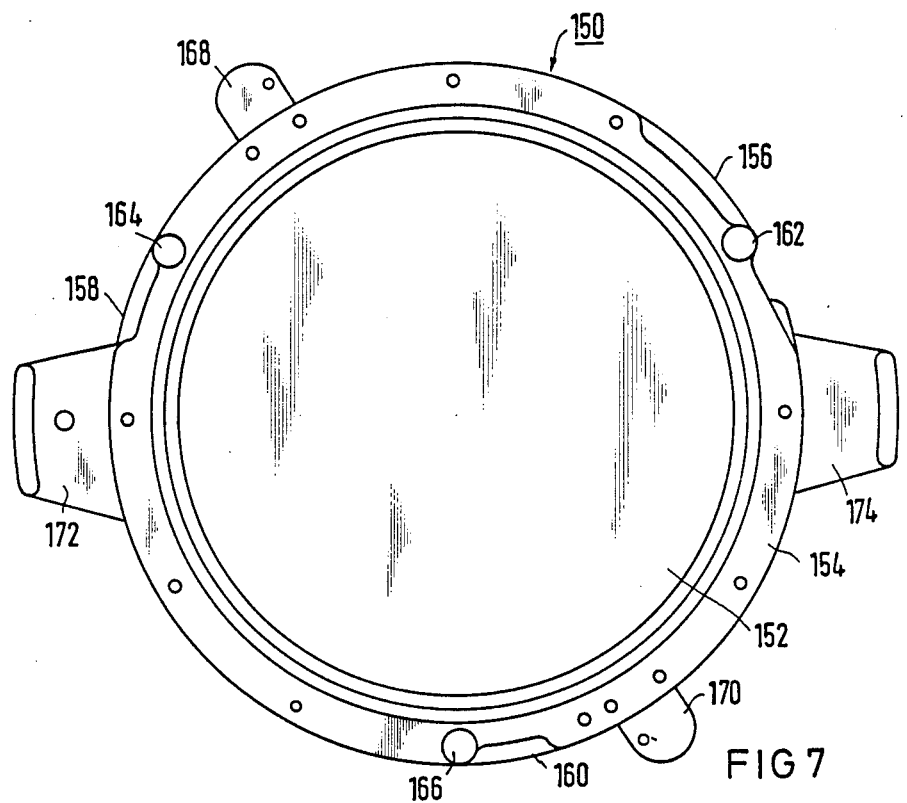
FIG. 7 is a bottom view of a medium energy collimator which is designated for being attached to a radiation detector according to FIG. 1.

FIG. 1 shows the face 10 of a radiation detector 12 of a scintillation gamma camera. The reference numeral 14 indicates the position of the scintillation crystal of the radiation detector 12. On the face 10 of the radiation detector 12 are mounted a first cleat 16, a second cleat 18 and a third cleat 20. The third cleat 20 is portion of a latch housing 22 which comprises a latch pin 24. The cleats 16 to 20 serve for cleating a collimator (e.g. according to FIGS. 5 and 7) to the face 10 of the radiation detector 12. The latch pin 24 is designated for latching the cleated collimator against rotation.

According to this invention each cleat 16–20 is associated with a collimator cleating detection means and also the latch pin 24 in latch housing 22 is associated with a collimator latching detection means.

Figure 2:
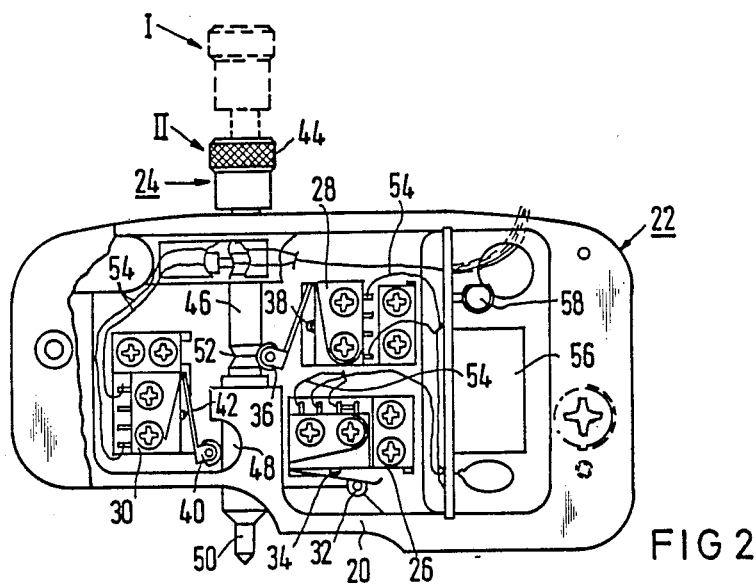
FIG. 2 is a top view of a latch comprising collimator latching detection means according to this invention.

As illustrated in FIG. 2 in the latch housing 22, which comprises the third cleat 20 and the latch pin 24 there are mounted a first microswitch 26, a second microswitch 28 and a third microswitch 30 in the indicated positions. The first microswitch comprises a switch lever 32 and a switch contact 34. In the shown position, the switch lever 32 does not depress the switch contact 34. The first microswitch 26 is in its released or off-position. The same can be stated with respect to the second microswitch 28 the switch lever 36 of which does not depress the switch contact 38. The third microswitch 30, however, is in a depressed or on-position, since its switch lever 40 depresses switch contact 42.

The first microswitch 26 in its released position detects that no collimator has been attached underneath the third cleat 20. In case of correctly attaching the collimator underneath cleat 20 the first microswitch 26 will be depressed.

The second microswitch 28 and the third microswitch 30 are activated by the latch pin 24. According to FIG. 2, latch pin 24 comprises a head portion 44, a first middle portion 46, a second middle portion 48 and an end portion 50. The latch pin 24 also includes a circular groove 52 between the first middle portion 46 and the second middle portion 48. Finally, the end portion 50 has a diameter which is smaller than the diameter of the first and second middle portions 46, 48.

According to FIG. 2 the latch pin 24 can be shifted between a first end position I and a second end position II. In the first end position I which is indicated in FIG. 2 by dotted lines, the latch pin 24 is in "open" position with respect to an attached collimator. In the second end position II which is depicted in FIG. 2 with solid lines, the latch pin 24 is in a "closed" position with regard to an attached collimator. In the "closed" position (second end position II) of the latch pin 24, switch lever 36 touches latch pin 24 in the circular groove 52. Therefore, the contact 38 of the second microswitch 28 is released. In contrast to this, the switch lever 40 of the third microswitch 30 touches the latch pin 24 on its second middle portion 48. Under these circumstances, the contact 42 of the third microswitch 30 becomes depressed.

In the "open" position (first end position I) of the latch pin 24, the switch lever 36 of the second microswitch 28 touches the second middle portion 48 of the latch pin 24. Now the contact 38 of the second microswitch 28 becomes depressed. Instead, the switch lever 40 of the third microswitch 30 touches the end portion 50 of the latch pin 24. Therefore, the contact 42 of the third microswitch 30 becomes released in the "open" position of the latch pin 24.

Figure 8:
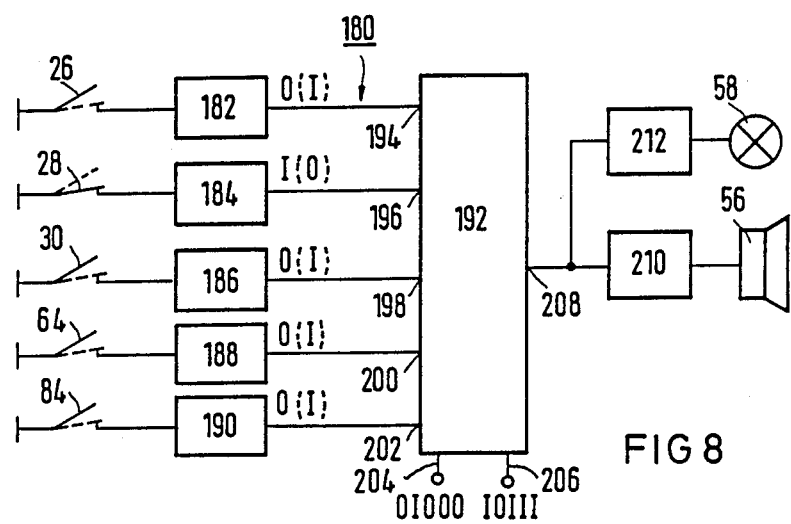
FIG. 8 is a block diagram of a logic circuit as part of collimator cleating and collimator latching detection means.

In FIG. 2 the signal lines for the first, second and third microswitches 26, 28, 30 are generally designated by 54. All three microswitches are connected by means of signal lines 54 with a logic circuit as illustrated in FIG. 8. The element 56 in FIG. 2 is a buzzer and the element 58 is an electroluminescence diode (LED).

Figure 3:
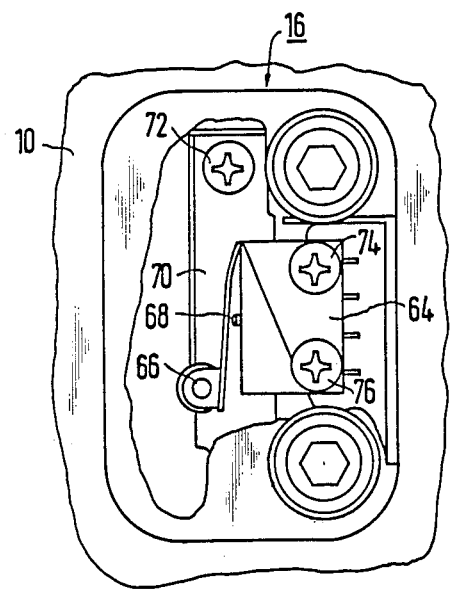
FIG. 3 is a top view of a cleat comprising collimator cleating detection means according to this invention.
Figure 4:
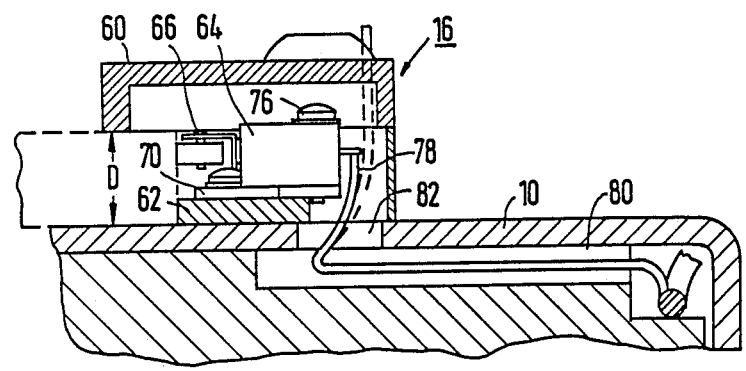
FIG. 4 is the cleat of FIG. 3 in a cross-section.

FIGS. 3 and 4 illustrate, for example the first cleat 16. However, the second cleat 18 has the same design. The cleat 16 has a cleat top 60 and a cleat bottom 62. The cleat bottom 62 is mounted at the face 10 of the radiation detector 12. There is a clearance D between cleat top 60 and face 10 of the radiation detector 12. The cleat 16 comprises a fourth microswitch 64 which includes a switch lever 66 and a switch contact 68. The fourth microswitch 64 is mounted by means of an adjustable plate 70 on the cleat bottom 62 of the first cleat 16. The element 72 is a mounting screw for the adjustable plate 70. The elements 74 and 76 are mounting screws for the fourth microswitch 64.

The fourth microswitch 64 is connected by means of signal leads 78 with the logic circuit as illustrated in FIG. 8. The signal leads 78 are fed to the logic circuit through a channel 80 inside the housing of the radiation detector 12 which channel 80 is connected with the interior of cleat 16 by means of a bore 82.

In the position shown in FIGS. 3 and 4 the switch lever 66 of the fourth microswitch 64 is in a position, where it does not depress the contact 68 of the microswitch. The microswitch 64 is in this released position when a collimator is not attached to the face 10 of the radiation detector 12.

As soon as a collimator is attached to the face 10 of the radiation detector 12 the part of the collimator which penetrates the clearance D under the cleat 16 (as indicated in FIG. 4 by dotted lines) depresses the switch lever 66 of the fourth microswitch 64. Under these circumstances, the switch contact 68 of the fourth microswitch 64 also becomes depressed.

The same happens with respect to a fifth microswitch 84 (indicated in FIG. 1) which is installed in the second cleat 18. This fifth microswitch 84 is also released as long as a collimator is not attached. As soon as the collimator becomes attached the fifth microswitch 84 is forced into the depressed position.

Figure 5:
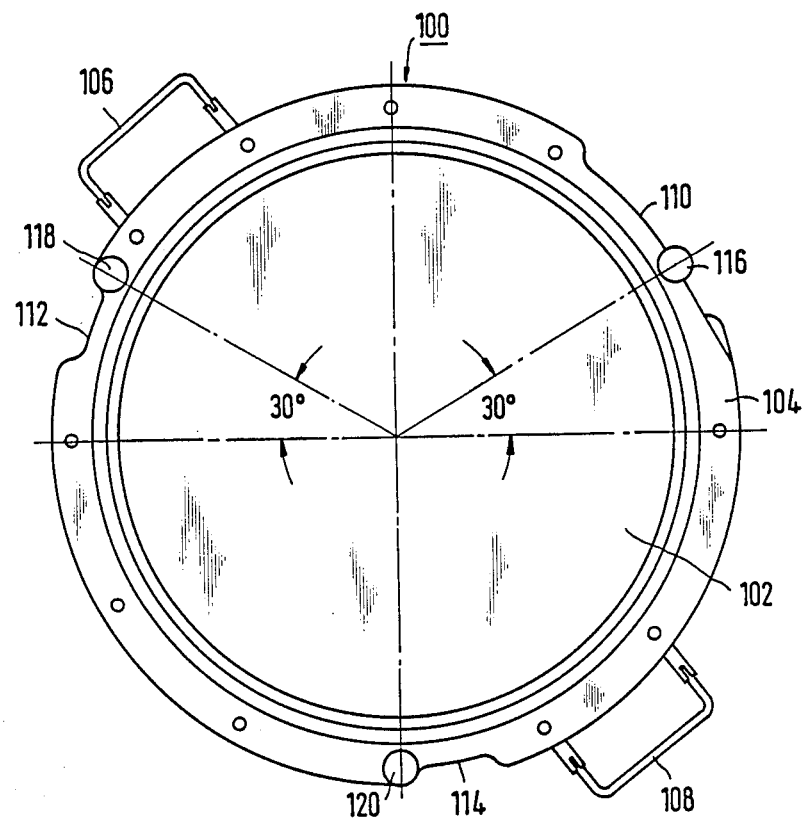
FIG. 5 is a bottom view of a low energy collimator designated for being attached to the face of a radiation detector according to FIG. 1.

FIG. 5 shows a low energy collimator 100, comprising a collimator core 102 and a collimator periphery 104. The collimator 100 also includes a first collimator handle 106 and a second collimator handle 108. The collimator periphery 104 furthermore contains a longer first recess 110 and a second and third shorter recesses 112 and 114. The collimator periphery 104 also comprises a first, a second and a third circular pieces 116, 118 and 120, which are placed close to the recesses 110, 112 and 114.

Figure 6:
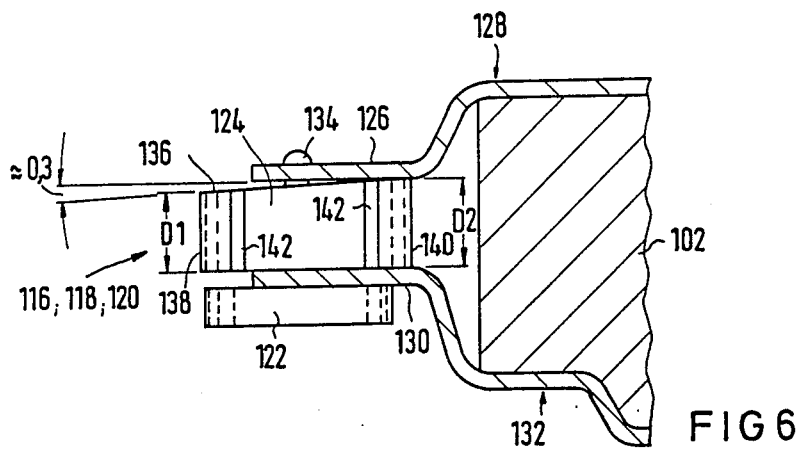
FIG. 6 is a partial cross-section of the collimator of FIG. 5 showing a rotary cam mounted at the collimator for wedging it in a cleat.

As can be seen from FIG. 6, each circular piece 116, 118 or 120 comprises a circular pad 122 and a rotary cam 124. The rotary cam 124 is rotatably mounted between the periphery portion 126 of the top spinning 128 of the collimator 100 and the periphery portion 130 of bottom spinning 132 of the collimator 110 by means of a holding screw 134 and circular pad 122. The rotary cam 124 comprises an inclined plane 136 which effects, that one portion 138 of the circumference of the rotary cam 124 has a thickness D1 which is smaller than the thickness D2 of another portion 140 of the circumference of the rotary cam 124. The angle of inclination of incline plane 136 with respect to the periphery portion 126 of top spinning 128 of collimator 100 is about 0.03′.

The collimator 100 will be attached to the face 10 of the radiation detector 12 in FIG. 1 as follows:

The collimator 100 is positioned above the radiation detector face 10 such that the recess 110 is above the latch housing 22, the recess 112 is above cleat 16 and the recess 114 is above the cleat 18. After placing the collimator 100 at the face 10 of the radiation detector 12 collimator 100 is rotated clockwise by means of handles 106 and 108 such that the circular pad 122 and the rotary cam 124 of each circular piece 116, 118 and 120 at the collimator periphery 104 penetrates the clearance D of each cleat 16, 18 and 20. While doing this, the first microswitch 26 in cleat 20, the fourth microswitch 64 in cleat 16 and the fifth microswitch 84 in cleat 18 become depressed. They so indicate that the collimator 100 has been correctly cleated in cleats 16, 18 and 20 on the face 10 of the radiation detector 12.

However, during rotating the collimator 10 for cleating also each rotary cam 124 due to friction rotates and becomes wedged in the clearance D of each cleat 16, 18 and 20. Each rotary cam 124 may also be rotated by means of a tool such as a screwdriver, via grooves 142 at the circumference of the rotary cam 124.

After having correctly cleated the collimator 100 the latch pin 24 has to be brought from its "open" position I into its "closed" position II. In this position the second microswitch 28 and the third microswitch 30 are in the switching positions as illustrated in FIG. 2. They so indicate that collimator 100 is also correctly latched.

Instead of low energy collimator 100, also a medium energy collimator 150 may be attached to the face 10 of the radiation detector 12. The medium energy collimator 150 again comprises a collimator core 152 and a collimator periphery 154. The collimator periphery 154 also has a longer recess 156 and two shorter recesses 158 and 160. The circular pieces 162, 164 and 166 have the same design as illustrated in detail in FIG. 6. Finally, the medium energy collimator 150 also comprises two handles 168 and 170 for rotation and a first and a second shifting access actuator 172 and 174.

FIG. 8 finally shows a schematic block diagram of a logic circuit 180 which is connected with the first, second, third, fourth and fifth microswitches 26, 28, 30, 64 and 84 as mentioned above.

As indicated in FIG. 8 the logic circuit 180 comprises a logic member 182, 184, 186, 188 and 190 for each microswitch 26, 28, 30, 64 and 84, respectively. Each logic member 182 to 190 generates at its output a logic ZERO (i.e. 0), when the corresponding microswitch 26, 28, 30, 64 and 84 is released (switch off). However, each logic member 182 to 190 produces at its output a logic ONE (i.e. 1), when the corresponding microswitch 26, 28, 30, 64 and 84 is depressed (switch on).

The logic circuit 180 further comprises a comparator 192 having five first inputs 194 to 202 and two second inputs 204 and 206. It also contains a signal output 208 which is connected with an actuating circuit 210 for the buzzer 56 and an actuating circuit 212 for the LED 58.

As can be seen from FIG. 8 one of the two second comparator inputs 204, 206, namely input 204 is fed with the logic number 01000. The other input 206 is supplied with a logic number 10111.

In case no collimator 100 or 150 has been attached to the face 10 of the radiation detector 12 all microswitches 26, 28, 30, 64 and 84 are in the positions as indicated in FIG. 8. The logic members 182 to 190 will produce the logic pattern 01000 as illustrated in FIG. 8. In case a collimator 100 or 150 has correctly been attached to the face 10 of the radiation detector 12 all microswitches 26, 28, 30, 64 and 84 will be in the opposite positions (indicated by dotted lines). The logic pattern will now be 10111.

incorrect cleating or latching of the collimator however, will generate logic patterns at the outputs of logic members 182 to 190 which are different from the logic pattern mentioned above.

The comparator 192 of logic circuit 180 compares the logic pattern at the outputs of the logic members 182 to 190 with the logic numbers 01000 and 10111 fed in via second comparator inputs 204 and 206. In case of occurrance of differences the comparator generates an output signal at comparator output 208. The comparator output signal triggers actuating circuits 210 and 212 for activating the buzzer 56 and the LED 58. Buzzer 56 starts to buzz and LED 58 starts to flash such detecting that a collimator had been incorrectly cleated and/or latched.

Having thus described the invention with particular reference to the preferred form thereof, it will be obvious to those skilled in the art to which the invention pertains, after understanding the invention, that various changes and modifications may be made therein without departing from the spirit and scope of the invention as defined by the claims appended hereto.

What is claimed is:

1. A device for attaching a collimator to a radiation detector, comprising
   a. a cleat means at the radiation detector for cleating the collimator to the radiation detector;

b. a latch means for latching the cleated collimator against rotation;
c. a collimator cleating detection means associated with the cleat means for detecting incorrect cleating of the collimator; and
d. a collimator latching detection means associated with the latch means for detecting incorrect latching of the collimator.

2. The device according to claim 1, wherein the cleat means comprises a number of cleats and the collimator cleating detection means including
   a. a cleat switch means for each cleat designated for being activated by the collimator during collimator cleating; and
   b. a logic circuit means connected with each cleat switch means for generating a detection signal when at least one cleat switch means has not been activated by the collimator during collimator cleating.

3. The device according to claim 1, wherein the latch means are movable between a first position, where the latch means does not latch the collimator and a second position, where the latch means latches the collimator and wherein the collimator latching detection means includes
   a. a first latch switch means for the latch means designated for being activated by the collimator during collimator cleating;
   b. a second latch switch means for the latch means designated for being activated by the latch means in the second latch means position; and
   c. a logic circuit means connected with the first and second latch switch means for generating a detection signal when one of the first and second latch switch means has been activated while the other one has not been activated.

4. The device according to claim 1, wherein
   a. the cleat means comprises a number of cleats;
   b. the collimator cleating detection means includes a cleat switch means for each cleat designated for being activated by the collimator during collimator cleating;
   c. the latch means are movable between a first position, where the latch means does not latch the collimator and a second position, where the latch means latches the collimator;
   d. the collimator latching detection means includes a latch switch means for the latch means designated for being activated by the latch means in the second latch position; and
   e. a logic circuit means connected with the cleat and latch switch means for generating a detection signal, when
      e1. at least one cleat switch means has not been activated by the collimator during collimator cleating; or
      e2. each cleat switch means has been activated by the collimator during collimator cleating while the latch switch means has not been activated.

5. The device according to claim 2, wherein the cleat switch means comprises a microswitch for each cleat which is released as long as no collimator has been cleated by the respective cleat.

6. The device according to claim 3, wherein the first latch switch means comprises a first microswitch which is released as long as no collimator has been cleated.

7. The device according to claim 3, wherein the second latch switch means comprises a second and a third microswitch wherein
   a. the second microswitch is depressed and the third microswitch is released when the latch means is in the first position; and
   b. the second microswitch is released and the third microswitch is depressed when the latch means is in the second position.

8. The device according to claim 7, wherein the second and third microswitches are depressed when the latch means is in a position between the first and second positions.

9. The device according to claim 7, wherein the latch means comprises a collimator latch pin mounted at the radiation detector and being movable between the first and second latch means positions, said latch pin having two middle portions comprising a first recess therebetween, and an end portion comprising a second recess, and wherein the second microswitch comprises a switch lever which in the first latch pin position touches the latch pin in the second middle portion thereby depressing the second microswitch; and wherein the third microswitch comprises a switch lever which in the first latch pin position touches the latch pin in the second recess thereby releasing the third microswitch.

10. The device according to claim 9, wherein in the second latch pin position the switch lever of the second microswitch touches the latch pin in the first recess while the switch lever of the third microswitch touches the latch pin at the second middle portion.

11. The device according to claim 9, wherein in a latch pin position between the first and second latch pin positions the switch levers of the second and third microswitches both touch the second middle portion of the latch pin.

12. The device according to claim 9, wherein the first recess of the latch pin is a circular recess.

13. The device according to claim 9, wherein the end portion of the latch pin has a smaller diameter than the first and second middle portions, thus forming the second recess.

14. The device according to claim 1, wherein the latch means comprising a collimator latch lock mounted at the radiation detector and a rotary cam mounted at the collimator for additionally wedging the collimator in the cleat means.

15. The device according to claim 14, wherein the collimator latch lock is shaped as a latch pin.

16. The device according to claim 1, wherein the collimator cleating and latching detection means comprises means for generating an accoustical alarm in case of incorrect cleating and/or latching.

17. The device according to claim 1, wherein the collimator cleating and latching detection means comprises means for generating an optical alarm in case of incorrect cleating and/or latching.

* * * * *